United States Patent [19]

Ebersole

[11] Patent Number: 4,458,014

[45] Date of Patent: Jul. 3, 1984

[54] SEROLOGICAL METHOD FOR THE IDENTIFICATION OF MICROORGANISMS

[75] Inventor: Jeffrey L. Ebersole, Westboro, Mass.

[73] Assignee: Forsyth Dental Infirmary for Children, Boston, Mass.

[21] Appl. No.: 338,644

[22] Filed: Jan. 11, 1982

[51] Int. Cl.³ .............. G01N 33/54; C12Q 1/04; C12N 11/06; C07G 7/00
[52] U.S. Cl. .................................. 435/7; 435/28; 435/29; 435/34; 435/180; 435/181; 436/531; 436/532; 436/547
[58] Field of Search .............. 435/7, 28, 29, 34, 39, 435/174, 177, 180, 181; 436/518, 531, 532, 547

[56] References Cited

U.S. PATENT DOCUMENTS

| 3,639,558 | 2/1972 | Csizmas et al. | 435/181 |
| 3,790,447 | 2/1974 | Hirata et al. | 435/7 |
| 4,016,043 | 4/1977 | Schuurs et al. | 435/7 |
| 4,379,135 | 4/1983 | Sasaki et al. | 435/34 X |

FOREIGN PATENT DOCUMENTS

| 2811228 | 9/1978 | Fed. Rep. of Germany | 435/7 |
| 54-119992 | 9/1979 | Japan | 435/7 |

OTHER PUBLICATIONS

Poxton I. R. Serological Identification of Bacteroides Species by an Enzyme-Linked Immunosorbent Assay, Journal of Clinical Pathology, vol. 32, 1979, (pp. 294–298).

Lambe, Jr., Determination of *Bacteroides melaninogenicus* Serogroups by Fluorescent Antibody Straining, Applied Microbiology, vol. 28, No. 4, 1974 (pp. 561–567).

Jack et al., The Immobilization of Whole Cells, Advances in Biochem. Eng. vol. 5, 1977 (pp. 126, 127, 143 & 144).

Primary Examiner—David M. Naff
Attorney, Agent, or Firm—Richard P. Crowley

[57] ABSTRACT

A rapid, specific, serological method for identification of microorganisms is carried out by immunizing a warm-blooded mammal with a killed microorganism to obtain an antisera, conjugating the antisera with an enzyme marker, bonding a microorganism to a solid support, adding the enzyme-conjugated antisera to the bonded microorganism in the presence of a color reactant and identifying the microorganism from the color reaction. Preferably, immunizing is carried out with two injections of about $10^9$ killed microorganisms each with the second injection being about 14 to 21 days after the first, and recovering the antisera about 14 to 21 days after the second injection.

27 Claims, No Drawings

SEROLOGICAL METHOD FOR THE IDENTIFICATION OF MICROORGANISMS

BACKGROUND OF THE INVENTION

In general, to determine the genus, species, subspecies or strain groups of an organism, laborious and expensive biochemical and physiological procedures have been utilized. Various immunological techniques have been used to identify organisms serologically. Bacterial agglutination, immunofluorescence or immuno-precipitin assays have all been employed for this purpose. Bacterial agglutination only can be used to identify pure culture isolates, is generally a subjective qualitative assay and often relies upon subtle differences in antibody titers to differentiate organisms. Immuno-precipitin assays again only can analyze pure culture isolates. The preparation and characterization of materials are time-consuming and interpretations of the results are strictly qualitative, subjective decisions. Immunofluorescence (IF) can be used to identify both pure culture isolates and the presence of an organism in a complex mixture of bacteria. The nature of IF requires the availability of a fluorescence microscope, which, in itself, can limit the usefulness of the technique. Preparing and reviewing individual slides for reaction are tedious procedures. The results from the IF are essentially qualitative and subjective. Also, the sensitivity of the IF has been shown to be significantly less than enzyme-linked immune assays.

Bacteroides species are common etiologic agents in human anaerobic infections (1). The black-pigmented Bacteroides, including *Bacteroides melaninogenicus* subsp. *intermedius, Bacteroides melaninogenicus* subsp. *melaninogenicus* and *Bacteroides gingivalis* have been implicated as pathogens in human periodontal disease (2-5). Likewise, *Bacteroides asaccharolyticus*, which may be similar to *B. gingivalis*, has been shown to predominate in periodontal lesions of beagle dogs (6,7) and the primate, *Macaca arctoides* (8).

Serological identification of various species of *B. melaninogenicus* has been reported using immunofluorescent antibodies (IF) directed to capsular antigens (9, 10, 11) or to whole organisms (8, 12, 13). Similarly, using soluble antigen preparations in immunoelectrophoretic and gel diffusion analyses, Reed and coworkers (14) showed serological differences between oral and normal *B. asaccharolyticus* strains, as well as among other species of black-pigmented Bacteroides. Other workers, using cell-surface, outer-membrane complex antigens, identified serological differences among the Bacteroides with an enzyme immunoassay (15). However, in these studies, some cross-reactions among oral and nonoral Bacteroides species were found. In order to obtain monospecific antisera, cross-adsorptions were necessary. Lambe (12) showed that *B. melaninogenicus* subsp. *intermedius, B. melaninogenicus* subsp. *melaninogenicus* and *B. melaninogenicus* subsp. *asaccharolyticus* (now *B. gingivalis*) from humans could be serologically identified by IF. Also, recently fluorescent antibody kits, for detecting the *B. fragilis* (Fluorotec-F) and *B. melaninogenicus* (Fluorotec-M) groups, have been produced commercially (12). However, Mouton and colleagues (16) have shown that human *B. gingivalis* is not identified by either of these reagents, while the Fluorotec-M does react with both *B. melaninogenicus* subsp. *intermedius* and *B. melaninogenicus* subsp. *melaminogenicus*. The association of these types of organisms in sites of periodontal breakdown generally has been determined using a predominant cultivatable flora approach.

Thus, there exists a need for a rapid, simple and effective method for the identification of microorganisms, particularly the identification of microorganisms from the oral cavity in the presence of complex bacterial mixtures of microorganisms.

SUMMARY OF THE INVENTION

The invention relates to a method for the serological identification of microorganisms and a kit assembly employed in such identification. In particular, the invention relates to the rapid, specific, serological identification of microorganisms, particularly from the oral cavity.

The method of identification of microorganisms provides for a rapid, simplified, specific identification of microorganisms, particularly oral microorganisms obtained from the oral cavity, and more particularly microorganisms obtained from lesions of periodontal disease. The method utilizes serological characteristics of the microorganisms, to permit the determination of genus, species, subspecies and strain groups of various microorganisms. The microorganisms to be identified may be from any source and can be identified from pure culture isolates or can be identified in a complex mixture of organisms obtained from a single sample by employing the method of the invention. In addition, not only qualitative, but quantitative analysis may be performed employing the method of identification, to determine the number or quantity of any one type of organism persent in a complex microbiological sample.

The method of identification overcomes the cumbersome and time-consuming nature of present techniques for the identification of microorganisms and permits the preparation of antisera, such that specificity for microorganisms can be induced without extensive cross-adsorption of the sera. The method of identification, the preparation of the antisera, the attaching of the microorganisms to the substrate, such as the wells of the plastic microtiter plate, as well as the specific development of the colorimetric reaction produced by the method, are unique and are an improvement over methods previously known to be employed in the method of identifying microorganisms.

The method of identification has been developed particularly for use in rapid, simple, specific identification of black-pigmented oral Bacteroides (BPB) from the oral cavity; however, the method of identification used to identify the presence of these organisms in complex bacterial mixtures from oral sites may be employed in the general identification of microorganisms from any source.

The invention comprises an enzyme-linked immunosorbent assay (ELISA) technique and kit for the identification of microorganisms. The method comprises injecting a warm-blooded mammal, such as a rabbit, with a killed microorganism, particularly a formalin-killed microorganism of known genus, species, subspecies or strain, to elicit antibodies in the serum of the mammal which are specific to the killed microorganism.

A microorganism-specific antisera is recovered from the mammal, and the gamma globulins of the antibody-containing serum is obtained, such as by salt fractionation. A known and unknown microorganism (that is, the microorganism to be identified) is then secured by bonding to a solid support, such as to the well of a microtiter plate, particularly a polymeric multiwell microtiter plate, such as a microtiter plate composed of a styrene polymer like polystyrene. The microorganisms are bonded by a fixative, such as a chemical fixative, such as an aldehyde like glutaraldehyde, to a plastic or polymeric plate support. The recovered, specific antiglobulin is conjugated with an enzyme marker, such as horseradish peroxidase or other enzyme marker material. The bonded microorganisms on the plate are then contacted with the enzyme-marked antiglobulin, and the plate support, with the antiglobulin and microorganism, is incubated for a short period of time, to effect the bonding of the enzyme-marked antiglobulin to the bonded microorganisms, such as for up to two hours at 25° C.; for example, 30 to 60 minutes. Unbonded antisera is removed, such as by washing with a saline solution. The reacted, bonded microorganism and antiglobulin are then contacted with a chemical substrate, to effect a color reaction, particularly with a substrate, such as N,N,N',N' tetramethylbenzidene, in the presence of a buffer like citric acid at a pH of 4.2 to 4.4, to provide a qualitative indication of the microorganisms. The color reaction can be viewed and the microorganism identified visually or the color reaction fixed, such as by the use of a thiocyanate solution, and examined colorimetrically, both to identify and quantify the microorganism. The unknown microorganism is identified by comparison with the reaction of the known microorganism.

The invention is useful in the clinical, qualitative determination of an organism in a bacterial sample on a primary isolation plate, to analyze isolated organisms from primary isolation plates to determine the predominant microorganism of the sample, to screen for the presence of a specific microorganism in bacteriological samples associated with disease lesions, and for the quantitative determination of a given organism in a complex bacterial sample.

In particular, a rapid method for specifying black-pigmented oral Bacteroides (BPB) is described. Species-specific rabbit antisera to *Bacteroides gingivalis, Bacteroides melaninogenicus* subsp. *intermedius* and *Bacteroides melaninogenicus* subsp. *melaninogenicus* were used in an enzyme-linked immunoadsorbent assay, to identify clinical isolates of black-pigmented Bacteroides from humans. The results showed an excellent agreement between the serotype of *B. gingivalis* and *B. melaninogenicus* subsp. *intermedius* and biochemical identification of the organism.

The procedure for the serologic identification of organisms utilizes certain theoretical aspects of the immune response, in order to provide a specific antisera which is the keystone of the assay. The antisera used in the technique is produced in rabbits. Specifically, microorganisms are isolated in pure culture, grown in media and harvested by centrifuging and washing with phosphate-buffered saline (PBS) containing 1 mM EDTA (PBSE). The organisms are then killed by treatment with 0.5% buffered formal saline for 16 to 18 hours. The bacteria is then washed and stored at 4° C. in PBSE. Rabbits were immunized in each hind footpad with 2 ml of an emulsion of $10^9$ organisms and incomplete Freund's adjuvant. 14 to 21 days later, the rabbit is boosted with 2 ml of $10^9$ organisms in incomplete Freund's adjuvant, with 1 ml given i.m. and the remaining material injected s.c. in the nape of the neck. Approximately 10 days to 2 weeks after the second injection, the rabbits are exsanguinated by cardiac puncture and the serum collected. In theory, this immunization regimen with formalinized microorgansisms should primarily elicit antibodies that are restricted in specificity to a limited array of immunodominant determinants in the bacteria. Thus, species-specific antisera can be produced with little difficulty. Gamma globulins are prepared by 40% $(NH_4)_2SO_4$ fractionation and conjugated with horseradish peroxidase, according to Nakane and Kawaoi (J. Histochem. Cytochem. 22:1084–1091). The antisera then can be stored frozen at −20° C.

The second part of the technique was accomplished by interfacing various procedures, to facilitate storage of antigen-coated plates for the analyses. Bacteria for serological identification either can be formalinized organisms, bacteria scraped from agar plates and suspended in PBS or organisms from broth cultures that have been pelleted and resuspended in PBS. 50 μl of the organisms in suspension are added to wells of microtiter plates and centrifuged for 5 minutes at 2000 rpm. 50 μl of 0.5% glutaraldehyde are added and incubated for 15 minutes at room temperature, to fix the organisms to the plates. The glutaraldehyde is removed by washing with PBS, and 200 μl of 0.1% BSA in 100 mM glycine buffer are added for 30 minutes at room temperature, to coat completely the plastic wells. The plates are then stored frozen, until they are analyzed with the conjugated antisera.

Enzyme-conjugated antisera is diluted in PBS containing 0.05% Tween 20 and is added in 100 μl to the microtiter wells and incubated at room temperature. It has been found that maximal binding of antibody takes place by 30 minutes of incubation. N,N,N',N' tetramethylbenzidene (TMB) is used as a substrate for the enzyme conjugate. The TMB is dissolved in glacial acetic acid at 15 mg/ml and stored frozen. For the assay, TMB is diluted 1:50 in 0.1M citrate buffer, pH 4.4, and 30% $H_2O_2$ added at a level of 1 μl/ml of TMB solution. 100 μl of the substrate are added to each well, and maximum color develops in 10 to 20 minutes. The reaction is stopped by the addition of 20 μl of 75 mM NaSCN. The resulting blue color can be analyzed colorimetrically with a bimodal absorbence peak at 380 nm and 620 nm. The greatest differentiation appears to reside at 380 nm. Antigen reactions thus can be scored as positive or negative, or the extent of color can be compared to a standard reference bacteria curve which was used in coating the plates.

In general, only immunofluorescence (IF) can be used as an alternative method for certain of the capabilities of this enzyme assay. IF can be used to identify serologically pure cultures of organisms. The IF technique also can be used to show the presence of an organism in a complex mixture of bacteria. However, the IF procedure is strictly a subjective procedure and cannot be used to quantitate the level of any one organism in a mixture. Also, the IF procedure is much slower than the ELISA, as well as considerably more laborious for identification of large numbers of isolated organisms.

A typical kit assembly for the serological identification of microorganisms by the method of the invention would include in combination a solid support surface, such as a test tube, glass slide, multiwell microtiter plates and the like, to which is bonded a single or a plurality of separate microorganisms of known genus, species, subspecies, strain to be used for comparative and identification purposes. The preferred support comprises a polymer, such as a styrene polymer, microtiter plate where the microorganisms have been bonded by the use of a fixative, such as a glutaraldehyde fixative. Another component of the kit assembly comprises a supply, such as in a vial container or the like, of an enzyme-coded antisera derived from a warm-blooded mammal, such as a rabbit, which antisera is specific for one or a plurality of microorganisms on the solid support.

A further component of the kit assembly includes a container of the enzyme substrate which provides a color reaction with the antisera. The specific antisera becomes bonded to the microorganisms on the solid support, to provide the coded known comparison. This known reactivity is used to compare the color reaction of the unknown microorgansims or microorganism mixture tested on the support. The preferred chemical substrate material would be a solution of N,N,N',N' tetramethylbenzidene.

Optionally, the kit assembly may contain other components, such as common laboratory chemicals or materials available to the user from other sources or their own laboratory supplies, such as a buffer for the color reactant, typically an aqueous citric-acid buffer solution, to provide a solution pH of 4.2 to 4.4 for the color reaction, a solution of a color fixative material, such as sodium thiocyanate, and a solution of hydrogen peroxide for the color reaction.

In operation of the kit assembly, the microtiter plate, as a support, is contacted with the antisera, the plate is incubated to bond the antisera to the microorganisms, and unbonded antisera is washed away with a saline solution, the bonded microorganism-coded antisera is then contacted with the chemical substrate, and the nature and extent of the color reaction is determined visually or by instrument. Optionally, the color reaction can be fixed by the addition of a fixative. The resulting known results then can be compared to the results achieved by the unknown microorganisms carried out in a similar manner, to identify and to quantify the unknown microorganisms by genus, species, subspecies, strain, etc.

The invention will be described for the purpose of illustration only with the serological identification of microbiological samples related to periodontal disease lesions; however, it is recognized and is within the scope of the invention that other microorganisms can be so identified employing the illustrative method and other modifications and changes made by a person skilled in the art.

DESCRIPTION OF THE EMBODIMENTS

Materials and Methods

Microorganisms—Bacteroides gingivalis strain 381 for immunization was grown in Mycoplasma broth base (BBL), supplemented with 5 µg/ml of hemin and 0.3 µg/ml menadione. The organisms were grown in an anaerobic chamber (80% $N_2$, 10% $H_2$ and 10% $CO_2$) at 37° C. The bacteria were harvested by centrifugation (12,000 g for 20 minutes) and washed three times with phosphate-buffered saline (0.02M phosphate) containing 1 mM ethylenediaminetetracetate (PBSE). The cells were finally resuspended in 0.5% buffered formal saline and incubated for 16 to 18 hours at room temperature in a rotator. The formalinized bacteria were washed three times with PBSE and stored at 4° C. in the same buffer.

A suspension of B. gingivalis, for examining parameters of the ELISA, was grown in broth as described above and prepared for testing by washing in PBS. B. gingivalis, B. melaninogenicus subsp. intermedius and B. melaninogenicus subsp. melaninogenicus were also grown on plates prepared from Trypticase soy agar (BBL) with 5% sheep blood and supplemented with 5 µg/ml hemin and 0.3 µg/ml menadione. The bacteria was grown anaerobically, harvested by scraping from the blood agar plates and suspended in PBS. Other organisms tested in the ELISA were grown as described in Table 1.

Antisera—Antibodies for B. gingivalis were prepared in rabbits by injection of formalinized bacteria. Rabbits were immunized with $10^9$ B. gingivalis emulsified in incomplete Freund's adjuvant (IFA; Difco) in the hind footpads. 14 to 21 days later, the rabbits were boosted with a similar preparation intramuscularly and subcutaneously in the nape of the neck. 14 to 21 days after the booster immunization, the rabbits were exsanguinated by cardiac puncture. The serum was obtained, following centrifugation of the clotted blood. Gamma globulins were prepared by $(NH_4)_2SO_4$ salt fractionation at 40% saturation. Following dialysis against PBS, the antiglobulins were stored at $-20°$ C. until tested.

Horseradish peroxidase (Type VI; Sigma) was conjugated to the anti-B. gingivalis globulins, according to the method of Nakane and Kawaoi (17). The conjugates were stored at $-20°$ C. at a 1:20 dilution in PBS containing 1% BSA (Sigma).

Serological Analysis with ELISA-The peroxidase-conjugated antiglobulins were used in an enzyme-linked immunosorbent assay using microtiter plates (Linbro). The substrate for the horseradish peroxidase was N,N,N'N' tetramethylbenzidene (TMB) (Sigma) (18). The TMB was dissolved at 15 mg/ml in glacial acetic acid and stored at $-20°$ C. For the enzyme assay, the TMB stock solution was diluted 1:50 in 0.05M sodium citrate buffer, pH 4.2. $H_2O_2$ was added to the TMB at a final concentration of 0.03%. This substrate solution was added to the microtiter plates (0.1 ml/well) and incubated for the colorimetric analysis. The enzyme-substrate reaction was stopped by addition of 20 µl of 75 mM NaSCN.

Attachment of Organisms to Microtiter Plates—For the serologic ELISA, a suspension of $1\times10^8$ and $5\times10^7$ formalized B. gingivalis, B. melaninogenicus subsp. intermedius, B. melaninogenicus subsp. melaninogenicus and Bacteroides gracilis strain 1084 was added to microtiter wells in 0.1 ml of PBS. The plates were centrifuged at 2000 rpm for 5 minutes (Sorvall GLC-2 centrifuge with HL-4 head). Either 50 µl of PBS or 0.5% glutaraldehyde were added to replicate wells and incubated at room temperature for 15 minutes. The supernatant was removed by washing with PBS, and 200 µl of 100 mM glycine buffer containing 0.1% BSA were added and incubated for 30 minutes at room temperature. The plates were then stored at $-20°$ C. until tested. A comparison of attachment of the organisms, with or without glutaraldehyde fixation, was then made. The results in Table 2 were obtained, following a 2-hour incubation with the enzyme-conjugated anti-B. gingivalis, and the resulting color change recorded. The results indicate that, at both dilutions of B. gingivalis organisms, the glutaraldehyde fixation significantly improved the resulting reaction. Testing the antisera against each of the other organisms gave negative reactions under all conditions.

Attachment of Organisms from Broth Cultures, Agar Plates or After Formalinization—To determine the optimal conditions for preparation of organisms to be used in the ELISA, three preparations were examined: broth cultures, organisms scraped from blood agar plates and organisms after formalin fixation. The *B. gingivalis* obtained by the three methods were suspended to various concentrations and used to coat the microtiter wells. The results in Table 3 indicate that each of the preparations were useful in the procedure; however, broth-grown organisms required two washes in PBS to reach maximum coating capabilities.

Sensitivity of Detection of Organisms in ELISA—Two procedures were used to determine the sensitivity of the ELISA for detecting the homologous microorganisms. Various concentrations of formalinized *B. gingivalis* in suspension were attached to the microtiter wells, to examine the maximum number of organisms necessary for a positive reaction to be detected. As shown in Table 4, approximately $10^5$ *B. gingivalis* added to the wells could be detected in the ELISA. Also, when *B. gingivalis* comprised a percentage of a mixture of formalinized organisms, including *Streptococcus sanguis*, *Actinomyces naeslundii* and *Capnocytophaga sputigena*, approximately $2-5 \times 10^5$ *B. gingivalis* in $10^6-10^8$ total organisms could be detected. Thus, the sensitivity of the procedure was comparable, using pure cultures or complex mixtures of organisms.

Antibody-Binding Kinetics in ELISA—To determine the optimal time of incubation with the enzyme-conjugated antisera, a time course study was performed. Antisera was incubated, with various concentration of *B. gingivalis* used to coat the ELISA plates. A substrate was added to the wells at intervals from 15 minutes to 4 hours, and the reaction intensity was scored. The results showed that, by 30 minutes of incubation, a maximum reaction was generated at each concentration of organism.

Absorbence Properties of the Reaction—In order to obtain a more quantitative estimate of the reaction, the spectrophotometric properties of the product were determined. The absorbence level of a standard reaction mixture was analyzed over a spectral range of 340 nm to 740 nm. The reaction exhibited a biphasic absorption pattern, with peaks at 340 to 380 nm and again at 620 nm. However, the optimal difference between the background and a known positive reaction was detected at 380 nm.

Specificity of Conjugated Antisera for Known Organisms—A variety of ATCC and isolates from other sources was used to determine the specificity of the anti-*B. gingivalis* conjugate. The data in Tables 5-9 show that this antiglobulin preparation reacted exclusively with known isolates of *B. gingivalis*, including two oral *B. asaccharolyticus* strains (BMD 1 and BMD 3) from periodontally diseased beagle dogs. In contrast, the antisera did not react with any other Bacteroides species, nor with a large selection of other oral and nonorol microorganisms. The relationship of the growth characteristics of the black-pigmented Bacteroides with antisera reactivity was also examined. *B. gingivalis* and *B. Melaninogenicus* subsp. *intermedius* were grown on supplemented blood agar for varying intervals of time. The organisms generally did not exhibit pigmentation in the colonies until 72 to 96 hours of growth. However, even when only white-colored colonies were detected (Table 10) at 2 days, the antisera identified the organisms. Similarly, organisms on plates that were stored at 4° C. for up to 2 weeks (that is, bacteria was nonviable) showed positive reactions with the antisera. The Bacteroides species were also cultured on laked blood agar, to enhance pigmentation, and the resulting antiserum reactions were as previously noted (Table 10).

Specificity of Conjugated Antisera for Clinical Isolates—To analyze further the specificity of the anti-*B. gingivalis* antisera, clinical isolates of various oral microorganisms were characterized phenotypically, as well as tested in the ELISA assay. The results (Table II) show that, similar to the known organisms previously described, the anti-*B. gingivalis* conjugate detects only *B. gingivalis*. Other oral Bacteroides, Fusobacteria species, Capnocytophage species and gram-negative asaccharolytic and saccharolytic rods were uniformly negative.

The method describes the use of an ELISA to identify serologically different species of black-pigmented Bacteroides. It was shown that the ELISA provides a rapid and reproducible assay for speciation of most black-pigmented Bacteroides. Rabbit antiglobulins produced to formalinized bacteria allowed easy access to specific antibody preparations. Previous studies have identified characteristics of different black-pigmented Bacteroides, including capsule formation (11) and capsular antigens (9, 10), that appear to be distinct antigenically among the species. These antigenic differences have been exploited by others to serogroup *B. melaninogenicus* subspecies (7, 8, 12, 19). In most of these studies, fluorescenated antisera was used for the detection system, and often some cross-reacting fluorescence was noted among the specimens. Similar findings of cross-reaction also have been shown in an enzyme immunoassay with soluble antigens from oral and non-oral Bacteroides species (15).

The significance of black-pigmented Bacteroides in humans has been established in many diseases (1). These organisms frequently have been associated with human periodontal disease (2-5). Recently, these organisms have been isolated from periodontal lesions in both beagle dogs (6, 7) and primates (8). Host responses to certain species of these organisms also have been identified in normal human serum (20). Furthermore, increased systemic immune responses to Bacteroides species have been shown in periodontal-disease patients (21, 22, J. L. Ebersole, D. E. Frey, M. A. Taubman, D. J. Smith, J. R. Wetherell and R. J. Genco, J. Dent. Res. 59:329, 1980). To substantiate further the association of Bacteroides species as possible etiological agents in periodontal disease, rapid methods for identifying these organisms in clinical samples were necessary. The serologic ELISA described herein can speciate the organisms in approximately 2 hours. The number of organisms can be determined by spectrophotometric analysis of the extent of color developed by a quantity of microorganisms. It was also shown that Bacteroides could be identified and quantitated in mixtures of microorganisms. Further, the usefulness of this technique has been delineated by speciating these organisms from primary isolation plates of samples from periodontal lesions (unpublished). The implementation of this procedure, as well as expansion of the technique to other microorganisms, should provide an improvement in the methods for describing the microflora associated with human periodontal disease.

TABLE 1

Growth Conditions for Microorganisms Tested in the Serologic ELISA

| Growth Conditions | Microorganism |
|---|---|
| Trypticase soy agar | Bacteroides gingivalis |
| 5% sheep blood | B. melaninogenicus ssp. intermedius |
| 5 μg/ml hemin | B. melaninogenicus ssp. melaninogenicus |
| 0.3 μg/ml menadione | B. loeschii |
| Anaerobic | B. socranskii |
| (80% $N_2$, 10% $H_2$, | B. corporis |
| 10% $CO_2$) | B. fragilis |
| | B. coagulans |
| | B. ureolyticus |
| | B. oralis |
| | B. asaccharolyticus |
| | Bacteroides D-8 |
| | Other Bacteroides species |
| Trypticase soy agar | Bacteroides gracilis |
| 5% sheep blood | "fusiform" Bacteroides |
| Anaerobic | Fusobacterium nucleatum |
| | F. gonidiaformans |
| | Other Fusobacterium species |
| | Capnocytophaga sputigena |
| | C. ochracea |
| | C. gingivalis |
| | Other Capnocytophaga species |
| | Wolinella recta |
| | W. succinogenes |
| | C. concisus |
| | Actinomyces naeslundii |
| | A. viscosus |
| | Streptococcus sanguis |
| | S. mutans |
| Trypticase soy agar | Eikenella corrodens |
| 5% sheep blood | Campylobacter sputorum ssp. bubulus |
| Microaerophilic | C. fetus ssp. intestinalis |
| | Campylobacter sputorum |
| | C. sputorum ssp. sputorum |
| | Actinobacillus actinomycetemcomitans |
| | Haemophilus aphrophilus |

TABLE 2

Effect of Glutaraldehyde Treatment on Fixation of Microorganisms in the ELISA

| Microorganism | Conc. (× $10^7$) | Treatment | Strength of Reaction | | | | | | |
|---|---|---|---|---|---|---|---|---|---|
| | | | $100^a$ | 200 | 400 | 800 | 1600 | 3200 | 6400 |
| B. gingivalis | 10 | PBS | $2+^b$ | 2+ | 2+ | 1+ | 1+ | — | — |
| | | $GLU^c$ | 3+ | 3+ | 3+ | 2+ | 2+ | 2+ | 1+ |
| | 5 | PBS | 1+ | 1+ | 1+ | 1+ | — | — | — |
| | | GLU | 3+ | 2+ | 2+ | 2+ | 1+ | 1+ | 1+ |
| B. mel. ssp. intermedius | 10 | PBS | — | — | — | — | — | — | — |
| | | GLU | — | — | — | — | — | — | — |
| | 5 | PBS | — | — | — | — | — | — | — |
| | | GLU | — | — | — | — | — | — | — |

$^a$Reciprocal dilution of anti-B. gingivalis conjugate
$^b$3+ - intense color with large amount of blue precipitate
2+ - intense color with some blue precipitate
1+ - detectable color with little to no precipitate
— - no detectable color above background which consisted of organisms and substrate solution. Each combination was performed in triplicate.
$^c$Denotes treatment of organisms with 0.5% glutaraldehyde

TABLE 3

Preparation of B. gingivalis for Attachment to ELISA Plates

| Preparation of Microorganism | Treatment | Concentration of Organisms Added Per Well | | | | |
|---|---|---|---|---|---|---|
| | | $10^8$ | $10^7$ | $10^6$ | $10^5$ | $10^4$ |
| Formalin-killed | | $+^a$ | + | + | + | — |
| Agar plates | | + | + | + | — | — |
| Broth cultures | $0^b$ | ± | ± | — | — | — |
| | $1^c$ | + | + | — | — | — |
| | 2 | + | + | + | — | — |
| | 3 | + | + | + | — | — |
| | 4 | + | + | + | — | — |
| | 5 | + | + | + | — | — |

$^a$+ - intense blue color reaction with precipitate
± - slight color range
— - no color compared to control. Each combination was performed in triplicate
$^b$Denotes organisms suspended in broth
$^c$Denotes number of washes of broth-grown organisms in PBS prior to attaching to plates

TABLE 4

Sensitivity of ELISA for Detection of B. gingivalis

| Microorganism | Concentration of Organisms to Wells | % B. gingivalis of Total Organisms | Antiserum Reaction |
|---|---|---|---|
| B. gingivalis | $10^8$ | | $+^a$ |
| | $10^7$ | | + |
| | $10^6$ | | + |
| | $10^5$ | | + |
| | $10^4$ | | — |
| | $10^3$ | | — |
| | $10^2$ | | — |
| | $10^1$ | | — |
| B. gingivalis | $10^8$ | 75 | + |
| S. sanguis$^b$ | | 50 | + |
| A. naeslundii$^b$ | | 25 | + |
| C. sputigena$^b$ | | 10 | + |
| | | 5 | + |
| | | 2 | + |
| | | 1 | + |
| | | 0.5 | + |
| | | 0.2 | — |
| | | 0.1 | — |
| | | 0.05 | — |
| | $10^7$ | 75 | + |
| | | 50 | + |
| | | 25 | + |
| | | 10 | + |
| | | 5 | + |
| | | 2 | + |
| | | 1 | — |
| | | 0.5 | — |
| | | 0.2 | — |
| | | 0.1 | — |
| | | 0.05 | — |
| | $10^6$ | 75 | + |
| | | 50 | + |
| | | 25 | + |
| | | 10 | — |
| | | 5 | — |
| | | 2 | — |
| | | 1 | — |
| | | 0.5 | — |
| | | 0.2 | — |

TABLE 4-continued

Sensitivity of ELISA for Detection of B. gingivalis

| Microorganism | Concentration of Organisms to Wells | % B. gingivalis of Total Organisms | Antiserum Reaction |
|---|---|---|---|
| | | 0.1 | − |
| | | 0.05 | − |

[a] + - blue color with precipitate
− - no detectable color. Each combination tested in duplicate
[b] Organisms comprised equal portions of mixture to obtain final concentration with B. gingivalis

TABLE 5

Specificity of Conjugated Antiglobulins to B. gingivalis, B. mel. subsp. intermedius and B. mel. subsp. melaninogenicus for Black-Pigmented Bacteroide Species

| Microoganism | Designation | Bg[a] | Bmi[b] | Bmm[c] |
|---|---|---|---|---|
| Bacteroides gingivalis | 381 | + | − | − |
| | ATCC 33277 | + | − | − |
| | 1223 | + | − | − |
| | 299 | + | − | − |
| | 376 | + | − | − |
| B. asaccharolyticus | BMD1 (dog) | + | − | − |
| | BMD3 (dog) | + | − | − |
| | 536B | − | − | − |
| B. mel. subsp. intermedius | 581 | − | + | − |
| | 377 | − | + | − |
| | ATCC 25611 | − | + | − |
| | A663 | − | + | − |
| | A666 | − | + | − |
| | A451 | − | + | − |
| | A450 | − | + | − |
| | A453X | − | + | − |
| | 8944 | − | − | − |
| B. mel. subsp. melaninogenicus | 287 | − | − | + |
| | 295 | − | − | + |
| B. loeschii | ATCC 15930 | − | − | − |
| B. socranskii | 10043 | − | − | − |
| B. corporis | 9342 | − | − | − |
| | 12530 | − | − | + |

[a] Anti-B. gingivalis conjutate
[b] Anti-B. melaninogenicus subsp. intermedius conjugate
[c] Anti-B. melaninogenicus subsp. melaninogenicus conjugate

TABLE 6

Specificity of Conjugated Antiglobulins to B. gingivalis, B. mel. subsp. intermedius, and B. mel. subsp. melaninogenicus for Other Bacteroides species

| Microorganism | Strain Designation[a] |
|---|---|
| B. oralis | ATCC 33321, A630, A647 |
| B. gracilis | 1084, A304A, A416, A311A, A420, 1083 1087, 404, 406, 402, 401, A117 |
| B. fragilis | 8708 AP |
| B. coagulans | A635, A690 |
| B. ureolyticus | A523, VPI 7814 |
| Bacteroides D8 | A654, A628, A622, A624 |
| "fusiform" Bacteroides | 338, 2083 |

[a] All strains tested were negative for reactivity with anti-B. gingivalis, B. mel. subsp. intermedius, and B. mel. subsp. melaninogenicus

TABLE 7

Specificity of Conjugated Antiglobulins to B. gingivalis, B. mel. subsp. intermedius, and B. mel. subsp. melaninogenicus for Fusiform-Shaped Bacteria

| Microorganism | Strain Designation[a] |
|---|---|
| Fusobacterium nucleatum | ATCC 25586, 364, 397, 392, 497, ATCC 10953, 398 |
| F. gonidiaformans | ATCC 25563B |
| Capnocytophaga sputigena | 4 |
| C. ochracea | 6, 25 |
| C. gingivalis | 27 |

[a] All strains tested were negative for reactivity with anti-B. gingivalis, B. mel. subsp. intermedius and B. mel. subsp. melaninogenicus

TABLE 8

Specificity of Conjugated Antiglobulins to B. gingivalis, B. mel. subsp. intermedius, and B. mel. subsp. melaninogenicus for Gram-Negative Asaccharolyti Bacteria

| Microorganism | Strain Designation[a] |
|---|---|
| Eikenella corrodens | 373, 1073, 479, 1078, ATCC 23834 |
| Wolinella recta | 371, 285, 1219, A435A, A425B, A411 A402, 0110, 10279, 155 |
| Wolinella species | VPI 9584, VPI 10296, VPI 10656 |
| Campylobacter concisus | 484, 522 |
| Campylobacter species | 288 |
| C. sputorum ssp. sputorum | S17 |
| C. sputorum ssp. bubulus | 616 |
| C. fetus ssp. intestinalis | 1176 |

[a] All strains tested were negative for reactivity with anti-B. gingivalis, B. mel. subsp. intermedius and B. mel. subsp. melaninogenicus

TABLE 9

Specificity of Conjugated Antiglobulins to B. gingivalis, B. mel. subsp. intermedius, and B. mel. subsp. melaninogenicus for Gram-Negative Saccharolyti and Gram-Positive Bacteria

| Microorganism | Strain Designation[a] |
|---|---|
| Actinobacillus actinomycetemcomitans | Y4, ATCC 29522, ATCC 29524, ATCC 29523 NCTC 9710 |
| Hemophilus aphrophilus | NCTC 5906, ATCC 13252, ATCC 19145 |
| Actinomyces naeslundii | I |
| A. viscosus | T14 V, T14 AV |
| Streptococcus sanguis | 254 |
| S. mutans | Ingbritt, 6715, GS5, LM7 |
| Selenomonas sputigena | 5 |

[a] All strains tested were negative for reactivity with anti-B. gingivalis, B. mel. subsp. intermedius and B. mel. subsp. melaninogenicus

TABLE 10

Effect of Growth Conditions on ELISA Identification of Bacteroides Species

| Micro-organism | Growth Media | Interval[a] | Antiserum Reaction Bg[b] | 3mi[c] |
|---|---|---|---|---|
| B. gingivalis | HK Plates[d] | 2 days | ± | − |
| | HK Plates | 4–6 days | + | − |
| | HK Plates | 4–6 days 4° C. 1 week[e] | + | − |
| | HK Plates | 4–6 days 4° C. 2 weeks | ± | − |
| | Laked Blood Plates | 4–6 days | + | − |
| B. mel. subsp. intermedius | HK Plates | 2 days | − | − |
| | HK Plates | 4–6 days | − | − |
| | HK Plates | 4–6 days 4° C. 1 week | − | − |
| | HK Plates | 4–6 days 4° C. 2 weeks | − | − |
| | Laked Blood | 4–6 days | | |

TABLE 10-continued
Effect of Growth Conditions on ELISA Identification of Bacteroides Species

| Microorganism | Growth Media | Interval[a] | Antiserum Reaction Bg[b] | Bmi[c] |
|---|---|---|---|---|
| | Plates | | | |

[a]Interval of growth anaerobically at 37° C.
[b]Anti-B. gingivalis conjugate
[c]Anti-B. melaninogenicus subsp. intermedius conjugate
[d]HK denotes 5% sheep blood agar plates supplemented with hemin and menadione
[e]Organisms grown anaerobically at 37° C. for 4-6 days and subsequently stored in cold room for the described interval before testing.

TABLE 11
Specificity of Conjugated Antiglobulins to B. gingivalis, B. mel. ssp. intermedius and B. mel. ssp. melaninogenicus for Clinical Isolates

| Microorganism | No. Isolates Tested | No. Positive in ELISA Bg[a] | Bmi[b] | Bmm[c] | % Detected Bg | Bmi | Bmm |
|---|---|---|---|---|---|---|---|
| Bacteroides gingivalis | 103 | 103 | 0 | 0 | 100 | 0 | 0 |
| B. mel. ssp. intermedius | 169 | 4 | 160 | 0 | 2 | 95 | 0 |
| B. mel. ssp. melaninogenicus | 14 | 1 | 0 | 5 | 7 | 0 | 36 |
| Fusobacterium species | 23 | 0 | 0 | 0 | 0 | 0 | 0 |
| Capnocytophaga species | 5 | 0 | 0 | 0 | 0 | 0 | 0 |
| Other Gram-Negative asaccharolytic rods | 35 | 0 | 0 | 0 | 0 | 0 | 0 |
| Other Gram-Negative saccharolytic rods | 10 | 0 | 0 | 0 | 0 | 0 | 0 |

[a]Anti-B. gingivalis conjugate
[b]Anti-B. melaninogenicus subsp. intermedius conjugate
[c]Anti-B. melaninogenicus subsp. melaninogenicus conjugate

REFERENCES

1. Gorbach, S. L. and Bartlett, J. G., 1974, Anaerobic Infections, N. Engl. J. Med. 290: 1177-1184, 1237-1245, 1289-1294
2. Tanner, A. C. R., Haffer, C., Bratthall, G. T., Visconti, R. A. and Socransky, S. S., 1979, A Study of the Bacteria Associated With Advancing Periodontitis in Man, J. Clin. Periodontal. 6: 278-307
3. Slots, J., 1979, Subgingival Microflora and Periodontal Disease, J. Clin. Periodontal. 6: 351-382
4. Spiegel, C. A., Hayduk, S. E., Minah, G. E., Krywolap, G. N., 1979, Black-Pigmented Bacteroides From Clinically Characterized Periodontal Sites, J. Periodontal Res., 14: 376-382
5. White, D. and Mayrand, D., 1981, Association of Oral Bacteroides with Gingivitis and Adult Periodontitis, J. Perio. Res., 16: 259-265
6. Kornman, K. S., Siegrist, B., Soskolne, W. A. and Nuki, I., 1981, The Predominant Cultivable Subgingival Flora of Beagle Dogs Following Ligature Placement and Metronidazole Therapy, J. Perio. Res., 16: 251-258
7. Syed, S. A., 1980, Characteristics of Bacteroides asaccharolyticus From Dental Plaques of Beagle Dogs, J. Clin. Microbiol. 11: 522-526
8. Slotts, J., Hausmann, E., Mouton, C., Ortman, L. F., Hammond, P. G. and Genco, R. J., 1980, The Relationship Between the Periodontal Microflora and Alveolar Bone Loss in Macaca arctoides, In, Anaerobic Bacteria, D. W. Lambe, Jr., R. J. Genco and K. J. Mayberry-Carson (eds), New York, Plenum Publishing Corp, pp. 109-121.
9. Mansheim, B. J., Solstad, C. A. and Kasper, D. L., 1978, Identification of a Subspecies-Specific Capsular Antigen From Bacteroides melaninogenicus subspecies asaccharolyticus by Immunofluorescence and Electron Microscopy, J. Infect. Dis. 138: 736-741
10. Mansheim, B. J. and Coleman, S. E., 1980, Immunochemical Differences Between Oral and Non-Oral Strains of Bacteroides asaccharolyticus, Infect. Immun. 27: 589-596
11. Okuda, K., Slots, J. and Genco, R. J., 198, Capsules of Black-Pigmented Bacteroides: Bacteroides gingivalis, Bacteroides asaccharolyticus and Bacteroides melaninogenicus subspecies, Infect. Immuno.
12. Lambe, D. W., Jr., 1974, Determination of Bacteroides melaninogenicus Sero-groups by Fluorescent Antibody Staining, Appl. Microbiol. 28: 561-567.
13. Weissfeld, A. S. and Sonnenwirth, A. C., 1981, Rapid Detection and Identification of Bacteroides fragilis and Bacteroides melaninogenicus by Immunofluorescence, J. Clin. Microbiol., 13: 798-800
14. Reed, M. J., Slots, J., Mouton, C. and Genco, R. J., 1980, Antigenic studies of Oral and Non-Oral Black-Pigmented Bacteroides strains, Infect. Immun., 29: 564-574
15. Poxton, I. R., 1979, Serological Identification of Bacteroides Species By an Enzyme-Linked Immunosorbent Assay, J. Clin, Pathol., 32: 294-298
16. Mouton, C., Hammond, P., Slots, J. and Genco, R. J., 1980, Evaluation of Fluoretec-M for Detection of Oral Strains of Bacteroides asaccharolyticus and Bacteroides melaninogenicus, J. Clin. Microbiol., 11: 682-686
17. Nakane, P. K. and Kawaoi, A., 1974, Peroxidase-Labeled Antibody: A New Method of Conjugation, J. Histochem. Cytochem., 22: 1084-1091
18. Mesulam, M.-M., 1978, Tetramethylbenzidene for Horseradish Peroxidase Neurohistochemistry: A Non-carcinogenic Blue Reaction Product With Superior Sensitivity for Visualizing Neutral Afferents and Efferents, J. Histochem. Cyctochem., 26: 106-107
19. Griffin, M. H., 1970, Fluorescent Antibody Techniques in the Identification of the Gram-Negative Non-sporeforming Anaerobes, Health Lab. Sci., 7: 78-83
20. Hofstad, T., 1974, Antibodies Reacting With Lipopolysaccharides From Bacteroides melaninogenicus, Bacteroides fragilis, and Fusobacterium nucleatum in Serum From Normal Human Subjects, J. Infect. Dis., 129: 349-352
21. Mouton, C., Hammond, P. G., Slots, J. and Genco, R. J., 1981, Serum Antibodies to Oral Bacteroides asaccharolyticus (Bacteroides gingivalis): Relationship to Age and Periodontal Disease, Infect. Immun., 31: 182–192

22. Lehner, T., Wilton, J. M. A., Ivanyi, L. and Manson, J. D., 1974, Immunological Aspects of Juvenile Periodontitis (Periodontosis), J. Perio. Res., 9: 261–272

What is claimed is:

1. A method for the serological identification of microorganisms, which method comprises:
    (a) injecting a warm-blooded mammal with a killed microorganism in an immunization regimen of only a first and a second injection, the second injection given within about 14 to 21 days after the first injection, each injection containing about $10^9$ killed microorganisms, to elicit antibodies in the serum of the mammal that are specific to the immunodeterminants of the microorganism;
    (b) recovering from the mammal in about 14 to 21 days after the second injection a microorganism-specific antisera without need for extensive cross adsorption of the sera;
    (c) securing separately a known and unknown microorganism to a solid support by bonding the respective microorganisms to the solid support in the presence of a fixative;
    (d) conjugating the specific antisera with an enzyme marker material to provide enzyme-conjugated antisera;
    (e) contacting the bonded microorganisms on the solid support with the enzyme-conjugated antisera;
    (f) incubating the solid support of the microorganisms, the incubation carried out in a time of less than about two hours, to bond the enzyme-conjugated antisera to the microorganism bonded to the solid support;
    (g) removing unbonded enzyme-conjugated antisera from the solid support;
    (h) reacting the microorganism-bonded, enzyme-conjugated antisera on the solid support with a chemical substrate, to develop a color reaction between the chemical substrate and the enzyme-conjugated antisera; and
    (i) identifying the unknown microorganism by observing the nature of the color activity in comparison to the color activity of the reaction with the known microorganism.

2. The method of claim 1 wherein the warm-blooded mammal comprises a rabbit.

3. The method of claim 1 wherein the killed microorganism comprises a formalin-killed microorganism.

4. The method of claim 1 which comprises employing glutaraldehyde as a fixative to bond the microorganism to the solid support.

5. The method of claim 1 which comprises reacting gamma globulin in the antisera with horseradish peroxidase as an enzyme marker to provide the enzyme-conjugated antisera.

6. The method of claim 1 which comprises employing N,N,N',N' tetramethylbenzidene as the chemical substrate, to develop a color reaction between the N,N,N',N' tetramethylbenzidene and the bonded enzyme-conjugated antisera.

7. The method of claim 1 which comprises colorimetrically analyzing the color of the color reaction developed to identify the microorganism.

8. The method of claim 7 which comprises colorimetrically analyzing the color reaction developed by employing an absorption peak at about 380 nm.

9. The method of claim 1 wherein known microorganisms of selected genus, species, subspecies or strains thereof are separately attached to each of a plurality of wells in a polymeric microtiter plate as the solid support.

10. The method of claim 9 which includes employing a styrene polymer microtiter plate as the solid support.

11. The method of claim 1 which includes fixing the color reaction occurring by the addition of a color fixative within a defined time period after the reaction.

12. The method of claim 11 which includes employing N,N,N',N' tetramethylbenzidene as the chemical substrate and employing sodium thiocyanate as a color fixative, the color fixative added within about 30 minutes after the color reaction.

13. The method of claim 1 wherein the killed microorganism comprises formalin-killed microorganisms from the oral cavity of a patient.

14. The method of claim 1 wherein the killed microorganism comprises formalin-killed black-pigmented Bacteroides.

15. The method of claim 1 which includes recovering the specific gamma globulins by salt fractionation of the antisera.

16. A method for the serological identification of microorganisms, which method comprises:
    (a) injecting a rabbit with a formalin-killed microorganism in an immunization regimen of only a first and a second booster injection, each injection containing about $10^9$ killed microorganisms, the injections spaced apart by 14 to 21 days to elicit antibodies in the serum of the rabbit that are specific to the immunodeterminants of the microorganism;
    (b) recovering from the rabbit in about 14 to 21 days after the second booster injection a microorganism-specific antisera without the need for extensive cross adsorption of the sera;
    (c) securing separately a known and an unknown microorganism to a solid polymeric microtiter plate support, by bonding the respective microorganisms to the solid support in the presence of glutaraldehyde as a fixative;
    (d) conjugating the specific antisera with horseradish peroxidase as an enzyme-marker material to provide enzyme-conjugated antisera;
    (e) contacting the bonded microorganisms on the solid support with the enzyme-conjugated antisera;
    (f) incubating the solid support of the microorganisms, to bond the enzyme-conjugated antisera to the microorganism bonded to the solid support;
    (g) washing unbonded enzyme-conjugated antisera from the solid support;
    (h) reacting the microorganism-bonded enzyme-conjugated antisera on the solid support with N,N,N',N' tetramethylbenzidene as a chemical substrate, to develop a color reaction between the chemical substrate and the enzyme-conjugated antisera; and
    (i) identifying the unknown microorganism by observing the nature of the color activity in comparison to the color activity of the reaction with the known microorganism.

17. The method of claim 16 which includes fixing the color reaction developed by adding, within 30 minutes from the time of the maximum color reaction, a fixing amount of sodium thiocyanate.

18. The method of claim 17 which includes colorimetrically analyzing the color developed, to identify the microorganism genus, species, subspecies or strain.

19. The method of claim 16 which includes employing a styrene polymer microtiter plate as the solid support.

20. The method of claim 16 wherein the killed microorganism comprises formalin-killed microorganisms from the oral cavity of a patient.

21. The method of claim 16 which includes incubating the solid support for a period of two hours or less.

22. The method of claim 16 which includes carrying out the color reaction in the presence of a buffering agent at a pH of about 4.2 to 4.4.

23. The method of claim 22 which includes adding a citric-acid solution as a buffering agent.

24. A ket assembly for the serological identification of microorganisms, which kit comprises in combination:
- (a) a solid support composed of a polymeric microtiter plate having bonded to the wells thereof, by a glutaraldehyde fixative, a plurality of known microorganisms by defined genus, species, subspecies or strain;
- (b) a horseradish peroxidase-conjugated microorganism specific antisera derived from a rabbit injected with a formalin-killed known microorganism in an immunization regiment of only two injections, each injection containing about $10^9$ killed microorganisms, the injections spaced apart by 14 to 21 days;
- (c) a chemical substrate which comprises a container of an N,N,N',N' tetramethylbenzidene solution; and
- (d) a buffering agent to provide for a buffering action at a pH of 4.2 to 4.4, whereby, on adding the antisera to the bonded microorganism on the support in the presence of the chemical substrate, the microorganism can be identified by the nature of the color reaction.

25. The kit of claim 24 which includes a container of a color fixative to fix the color of the color reaction.

26. The kit of claim 24 wherein the solid support comprises a styrene polymer microtiter plate containing a plurality of separate known microorganisms, each bound to the surface of separate wells of the microtiter plates.

27. The kit of claim 24 wherein the solid support contains known microorganisms of black-pigmented Bacteroides.

* * * * *